United States Patent [19]

Chandler et al.

[11] Patent Number: 5,495,027

[45] Date of Patent: Feb. 27, 1996

[54] PREPARATION OF N-ACETYL NEURAMINIC DERIVATIVES

[75] Inventors: Malcolm Chandler; Niall G. Weir, both of Greenford, Great Britain

[73] Assignee: Biota Scientific Management Pty. Ltd., Glen Iris, Australia

[21] Appl. No.: 240,766

[22] PCT Filed: Dec. 14, 1992

[86] PCT No.: PCT/EP92/02904

§ 371 Date: Jun. 14, 1994

§ 102(e) Date: Jun. 14, 1994

[87] PCT Pub. No.: WO93/12105

PCT Pub. Date: Jun. 24, 1993

[30] Foreign Application Priority Data

Dec. 17, 1991 [GB] United Kingdom ............... 9126725

[51] Int. Cl.$^6$ .................................................... C07D 309/28
[52] U.S. Cl. ............................................................. 549/424
[58] Field of Search ............................................... 549/424

[56] References Cited

FOREIGN PATENT DOCUMENTS 9116320  10/1991  WIPO.

OTHER PUBLICATIONS

Schreiner et al.; "Synthesis of some 2,3-didehydro-2-deoxysilalic acids . . ."; Liebigs Annalen Der Chemie, No. 2, Feb. 1991, pp. 129–134.

*Primary Examiner*—Nicky Chan
*Attorney, Agent, or Firm*—Bacon & Thomas

[57] ABSTRACT

Processes for the preparation of 4-substituted analogues of 5-acetylamino-2,3,5-trideoxy-D-glycero-D-galacto-non-2-enopyranosinic acid are described.

17 Claims, No Drawings

PREPARATION OF N-ACETYL NEURAMINIC DERIVATIVES

The present application was filed under 35 U.S.C. §371 as the U.S. National Phase of International Patent Application No. PCT/EP92/02904, filed Dec. 14, 1992.

The present invention relates to a process for the preparation of derivatives of N-acetyl neuraminic acid. More particularly the invention relates to a process for the preparation of 5-acetamido-4-amino-2,3,4,5-tetradeoxy-D-glycero-D-galacto-non-2-enopyranosonic acid (the 4-amino analogue of DANA; also known as 5-(acetylamino)-4-amino-2,6-anhydro-3,4,5-trideoxy-D-glycero-D-galacto-non-2-enonic acid) and derivatives thereof and the preparation of intermediates for use in the process. Schreiner et. al. Ann. Chem 1991, 129–134 describe the preparation of the 4-amino analogue of DANA from the peracetylated methyl ester of sialic acid (peracetyl NANA methyl ester) by the route shown in Scheme 1.

PCT/AU91/00161 (publication no. WO91/16320) describes a number of derivatives of 5-acetamido 2,3,5-trideoxy-D-glycero-D-galacto-non-2-enopyranosonic acid (2,3-dideoxy-2,3-didehydro-N-acetyl-neuraminic acid; DANA) including the 4-amino analogue of DANA from the peracetylated methyl ester of DANA by a method similar to that of Schreiner et. al. with the exception that the peracetylated compound (3a) was reduced prior to deacetylation. The method is shown in Scheme 2.

A major problem with the known processes for preparing the 4-amino analogue of DANA lies in the fact that the conversion directly or indirectly of the compound (2) and any other compound with a leaving group in the 4-position with azide is not stereospecific and leads to significant amounts of the undesired β-isomer (3b) in addition to the desired α-isomer (3a). This leads to both reduced yields of the desired compound and to the need for chromatographic purification at this or a subsequent step in the synthesis.

We have now found that by careful selection of the azide source the conversion of (2) to (3a) can be effected with high stereospecificity.

The invention thus provides in a first aspect a method for the preparation of the compound of formula (I)

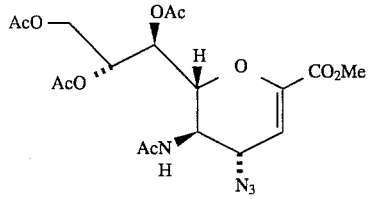

by reaction of the compound of formula (II)

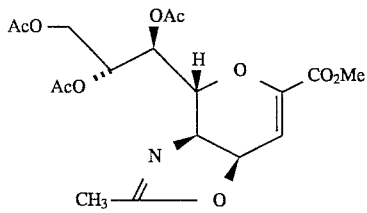

with trimethylsilylazide (TMSN$_3$).

It is currently believed that the reason for the stereospecificity is that the reaction generates HN$_3$ in situ; other reagents which generate HN$_3$ in situ are well known to those skilled in the art.

The reaction is effected in a protic solvent. Preferably the solvent is a C$_{1-8}$ alcohol in particular a hindered alcohol.

Hindered alcohols include for example isopropyl alcohol and, particularly, tert-butyl alcohol.

The reaction is conveniently carried out at a temperature of for example 0°–150° C., preferably at 15°–90° C. such as about 80° C. Conveniently the reaction will be effected at below the reflux temperature of the selected solvent.

The amount of TMSN$_3$ employed will generally be in the range of from about 1 to about 6 molar equivalents of the compound of formula (II), preferably 1.5 to 2 molar equivalents.

A significant problem also arises with the reduction of compounds such as (3a) and (4), there being a risk of undesired reduction of the 2,3-double bond in addition to reduction of the azido group. Such potential for over-reduction leads both to reduced yield and to the presence of by-products which necessitates more extensive purification procedures. We have now found that yield and purity of the 4-amino analogue of DANA can be improved by reducing the compound (4) or a protected derivative thereof in the presence of certain catalysts.

The invention thus provides in a second aspect a method for the preparation of the compound of formula (III)

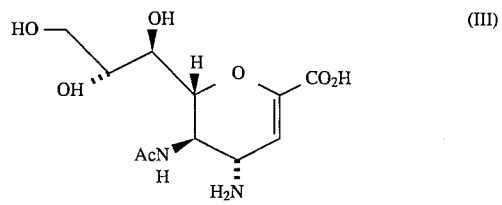

which comprises catalytic hydrogenation of a compound of formula (IV)

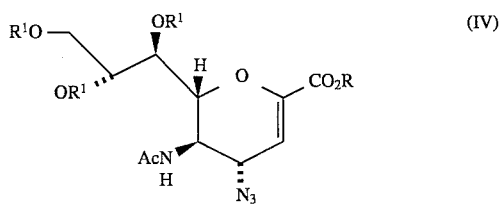

(wherein R is H or a C$_{1-4}$alkyl group and R$^1$ is H or a hydroxyl protecting group for example an acyl group such as acetyl) followed where required by hydrolysis.

The compound of formula (IV) may optionally be protected by any suitable hydroxyl protecting groups for example as described in 'Protective Groups in Organic Synthesis' by Theodora W. Green (John Wiley & Sons, 1981) which also describes methods for the removal of such groups. The compound of formula (IV) may be obtained by reacting a compound of formula (IIa) with trimethylsilylazide in a protic solvent.

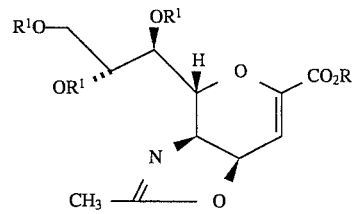

It will be appreciated by those skilled in the art that where R and/or R$^1$ in compound (IV) are other than hydrogen partial removal of the protecting groups and/or hydrolysis of the C$_1$-ester may occur during the reduction phase. However, upon hydrolysis all such partially hydrolysed compounds will be converted to the compound of formula (III).

The solvent for use in the reduction step may be either an aqueous solvent comprising water or a mixture water and any compatible organic solvent miscible with water or an organic solvent such as an ether, lower alcohol or the like. Preferably the solvent is water.

Preferably the catalyst is a poisoned catalyst but in particular a poisoned palladium catalyst. A particularly preferred catalyst is a Pd catalyst poisoned with lead, for example a Lindlar catalyst.

The reduction is conveniently carried out 0°–50° C., preferably at ambient temperature.

The hydrolysis may be effected by any suitable base and is preferably effected in an aqueous medium. Suitable bases include aqueous triethylamine, NaOH, $Na_2CO_3$ and the like. Where protecting groups are present appropriate deprotection agents known in the art may be employed.

In a preferred embodiment the invention comprises the preparation of the compound of formula (III) as defined herein from the compound of formula (II) by the steps of:

(a) reacting the compound of formula (II) with $HN_3$; to give a compound of formula (I)

(b) hydrolysing the compound of formula (I) to give a compound of formula (IV); and (c) hydrogenating the compound of formula (IV) in the presence of a poisoned catalyst followed by hydrolysis.

The 4-amino analogue of DANA is a potent inhibitor of the influenza virus both in vitro and in vivo and is thus useful in the treatment of viral infections such as influenza. (see for example WO91/16320).

The 4-amino analogue of DANA is also of use as an intermediate in the synthesis of other DANA derivatives which are inhibitors of the influenza virus (see for example WO91/16320).

The invention is illustrated by the following non-limiting examples. All temperatures are in °C.

Intermediate 1

A 3 liter 3-necked round bottomed flask equipped with a water condenser and presure equalised dropping funnel was charged with a solution of methyl 5-acetamido-2,4,7,8,9-penta-O-acetyl-D-glycero-D-galacto-2-nonulopyranosonate (peracetyl NANA methyl ester) (70 g) in dichloromethane (1050 ml). Trimethylsilyl trifluoromethanesulfonate (76 ml) was then added dropwise over 10 min. with stirring (magnetic stirrer) under an inert atmosphere of nitrogen. After the addition was complete the oil-bath temperature was raised over 25 min to ca. 50° C. After 4.5 h at reflux the reaction mixture was allowed to cool and poured into a vigorously stirred mixture of aqueous sodium hydrogen carbonate (1700 ml), ice (500 ml) and solid sodium hydrogen carbonate (80 g). After ca. 10 min. the solution was checked to confirm that it was still basic (pH=8) and the organic phase separated off. The aqueous phase was further extracted with dichloromethane (3 times 500 ml) and the combined extracts were treated with Norit ultra SX+charcoal, dried ($MgSO_4$) and evaporated in vacuo at 48°–50° C. (rotary evaporator) to give methyl 7,8,9-tri-O-acetyl-2,3-didehydro-2,3,5-trideoxy-4',5' -dihydro-2'-methyloxazolo[4,5-d]-D-glycero-D-talo-2-nonulopyranosidonate (52.5 g).

TLC: (Silica gel—Ethyl acetate: single spot Rf=0.55 (visualised with UV and ceric sulphate spray)

NMR: $\delta(CDCl_3)$ 2.15–2.0 4xs each 3H, 3.44 dd 1H, 3.81 s 3H, 3.96 dd 1H, 4.22 dd 1H, 4.60 dd 1H, 4.82 dd 1H, 5.44 m 1H, 5.64 m 1H, 6.38d 1H.

EXAMPLE 1

(i) A 3-necked round bottomed flask equipped with a water condenser and pressure equalised dropping funnel was charged with a solution of Intermediate 1 (7.8 g) in t-butanol (65 ml). Heating of the stirred solution (magnetic stirrer) to 80° C. was then commenced while azidotrimethylsilane (10.5 ml) was added dropwise over 3.5 h.

After a total of 4 h the reaction mixture was allowed to cool and poured into a vigorously stirred mixture of aqueous sodium hydrogen carbonate (350 ml), (chilled in an ice bath) and solid sodium hydrogen carbonate (10 g). After ca. 5 min. the solution was extracted with ethyl acetate (3 times 150 ml). The combined extracts were dried ($MgSO_4$) and evaporated in vacuo at 48°–50° C. (rotary evaporator) to give crude compound 3a, methyl 5-acetamido-7,8,9-tri-O-acetyl-4-azido-2,3-didehydro-2,3,4,5-tetradeoxy- D-glycero-D-galacto-2-nonulopyranosidonate (8.027 g).

TLC: (Silica gel—Methanol (1)/$CHCl_3$ (19)): Rf 0.1 (visualised with UV and Ceric sulphate spray)

NMR: $\delta(CDCl_3)$ 2.14–2.00 4xs each 3H, 3.82 s 3H, 3.88 m 1H, 4.21 m 1H, 4.5 m 2H, 4.64 dd 1H, 5.34 m 1H, 5.47 m 1H, 5.82 d 1H, 6.00 d 1H.

(ii) To a stirred solution of the product of step (i) (7.51 g) in dry methanol (17 ml) under an inert atmosphere of nitrogen was added 1% sodium methoxide (10 ml). The mixture was stirred at 21° C. for ca. 30 min. Dowex 50W×8 (H+) resin (ca 7 g) was added to adjust the pH to 7. The solvent was then filtered and the resin further washed with methanol (4×20 ml). The combined filtrates were evaporated under reduced pressure (rotary evaporator) at 48°–50° C. to give compound 4b, methyl 5-acetamido-4-azido-2,3 -didehydro-2,3,4,5-tetradeoxy-D-glycero-D-galacto-2-nonulopyranosidonate (5.03 g) as a buff foam.

TLC: (Silica gel—Methanol (1)/$CHCl_3$ (3)): Rf 0.025 (visualised with UV and Ceric sulphate)

NMR: $\delta(D_2O)$ 2.06 s 3H, 3.60–3.99 m 4H, 3.84 s 3H, 4.20–4.46 m 3H, 6.10 d 1H.

EXAMPLE 2

A 20 L 4 necked round-bottomed flask was equipped with a thermometer, an overhead air driven teflon stirrer and a condenser. The flask was immersed in a steam heated water bath. Hot water (50°) was circulated through the condenser. Nitrogen was passed through a combined inlet/outlet fitting at the top of the condenser to blanket the reaction and to flush any low boiling vapours through to a train of scrubbers containing sodium hydroxide solution (~2M) in two, and ceric ammonium nitrate solution (1% w/v) in the third final scrubber.

The reaction flask was charged with Intermediate 1 (1.5 kg) and tert.butanol (11 L). Trimethylsilyl azide (724 ml) was added and the stirred mixture was heated to reflux under the nitrogen blanket for 10 h. and left to cool overnight in the water bath.

A solution of sodium nitrite (300 g) in water (1.5 l) was added. The reaction mixture was cooled to <20°, the nitrogen blanketing was stopped and the top of the condenser was connected directly to the scrubber system.

Hydrochloric acid solution (~6M; 625 ml) was added dropwise over 1 h with continued cooling to maintain the temperature below 20°, and to control the gas evolution. The mixture was stirred for 2 h after gas evolution had ceased.

The mixture was transferred to a 50 L separator with ethyl acetate (8 L) and distilled water (8 L). The two layers were separated and the organic layer washed with water (2×8 L).

The combined aqueous layer was back extracted with ethyl acetate (5 L) and separated.

The combined organic layer was washed with sodium hydrogen carbonate solution (6% w/v, 2×8 L) and then with sodium chloride solution.

The separated organic layer was concentrated to a crystalline slurry (~1 vol) then the solid was collected by filtration, washed with water (2×2 L) and dried in vacuo to give compound 3a, methyl-5-acetamido-7,8,9-tri-O-acetyl-4-azido-2,3-didehydro-2,3,4,5-tetradeoxy-D-glycero-D-galacto-2-nonulopyranosidonate, monohydrate (1.32 kg). m.p. 89°.

N.M.R. $\delta(CDCl_3)$ 6.18(1H, d,9); 5.99(1H, d,3); 5.47(1H, m); 5.32 (1H, m); 4.67(1H, m); 4.46(1H, m); 4.19(1H, m); 3.93(1H, m); 3.82(3H, s); 2.15(3H, s); 2.18 (3H, s); 2.09(3H, s); 1.98(3H, s).

I.R. (Nujol) 3592(NH); 2120, 2087 (azide); 1752 (CO, acetate); 1732(CO, conj.ester); 1662cm$^{-1}$ (CO, CH$_3$CONH—).

Water content 4% (Karl Fischer method).

EXAMPLE 3

(i) A 3-necked round bottomed flask equipped with a gas inlet tube extending below the level of liquid and a gas outlet adaptor was charged with a solution of compound 4, prepared as described in Example 1, step (ii) (2.0 g) in water (50 ml). Lindlar catalyst (0.2 g) was then added and the flask flushed with nitrogen. Hydrogen was then bubbled through the vigorously stirred solution for 4 h. Additional catalyst (0.2 g) was then added at this stage and hydrogen bubbled through for a further 16 h. The catalyst was then removed by filtration through celite. The filter was washed with water (2 times 50 ml) and the combined filtrates evaporated under reduced pressure at 48°–50° C. (rotary evaporator) and the residue co-evaporated with methanol (3 times 50 ml) to give a solid found to be a mixture resulting from partial ester hydrolysis. This material was therefore fully de-esterified without further characterisation.

(ii) A solution of the product of step (i) (1.87 g) in water (20 ml) was stirred at 21° C. with triethylamine (5 ml) for 4 h. The resulting mixture was evaporated under reduced pressure at 48°–50° C. (rotary evaporator) followed by co-evaporation with methanol (2 times 100 ml) to give crude product (1.81 g).

(iii) A column of Dowex 2×8 (Cl$^-$) resin (100 g) was converted into it's hydroxide form with 2N sodium hydroxide solution (1.5 L). The resin was then washed free of hydroxide with water. Crude product from step (ii) (5.0 g) dissolved in water (250 ml) was then placed on the top of the column and eluted with water (400 ml). Following this the resin was eluted with 1N Acetic acid solution (2 L). Like fractions were combined and freeze dried to give the 4-amino analogue of DANA (2.45 g). A second slightly more coloured fraction was also obtained giving after treatment as above a further quantity of the title compound (0.53 g) the 4-amino analogue of DANA.

TLC: (Silica gel—nButanol (3)/Water (1)/Acetic Acid (1)): Rf=0.22 (visualised with UV, ninhydrin and ceric sulphate)

NMR: $\delta(D_2O)$ 2.05 s 3H, 3.6–4.0 m 4H, 4.2 m 1H, 4.36 m 2H, 5.69 d 1H.

UV: $(H_2O)_{max}$ 233130.7

EXAMPLE 4

A suspension of compound 3a (1 g), prepared as in Example 2, in water (10 ml) was treated with triethylamine (1.53 ml, added in 3 portions during 4½ h) and the solution was left at 20° for 24 h.

Lindlar catalyst (100 mg) was added and the mixture was stirred for 6 h in an atmosphere of hydrogen gas.

The catalyst was removed by filtration and the filter bed was washed with water (5× 2 ml). The combined filtrate and washings were concentrated to 3 ml then isopropanol (5 ml) was added portionwise. The cloudy solution was warmed and then allowed to cool, to deposit a crystalline solid. The solid was collected by filtration, washed with isopropanol (2×1 ml) and dried in vacuo to give the 4-amino analogue of DANA (0.44 g).

N.M.R. $\delta(D_2O)$ 5.62(1H, d,2); 4.40–4.25(2H, m); 4.18(1H, m); 4.05–3.50 (4H, m).

I.R. (Nujol) 3526, 3477, 3368, 3179(OH, NH); 1675(CO, amide); 1601 cm$^{-1}$(CO, CO$_2$H).

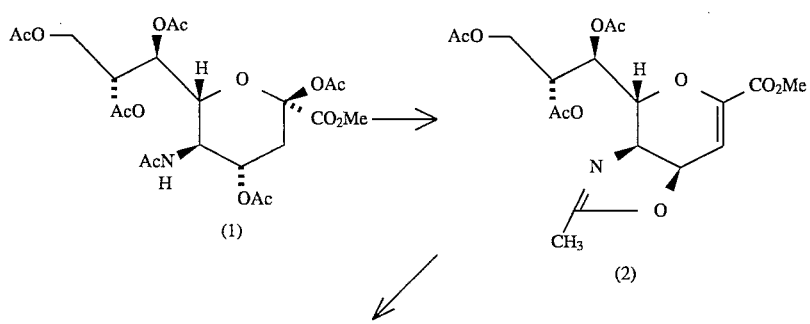

Scheme 1

-continued
Scheme 1
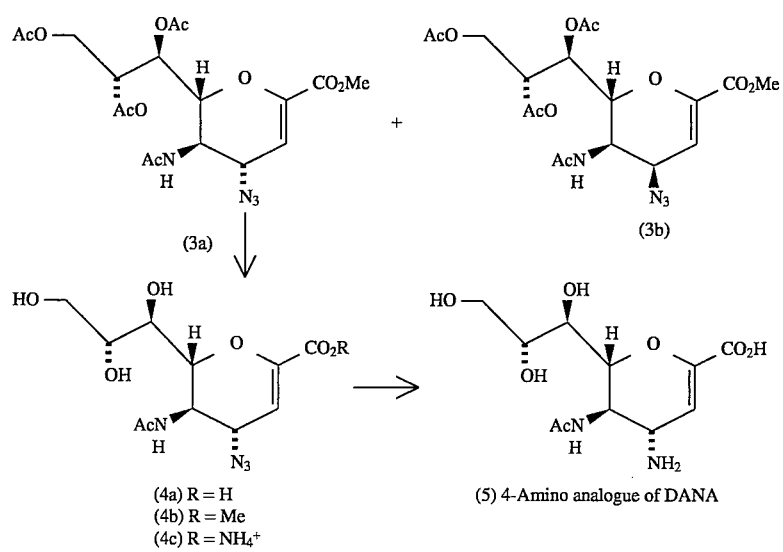
Scheme 2
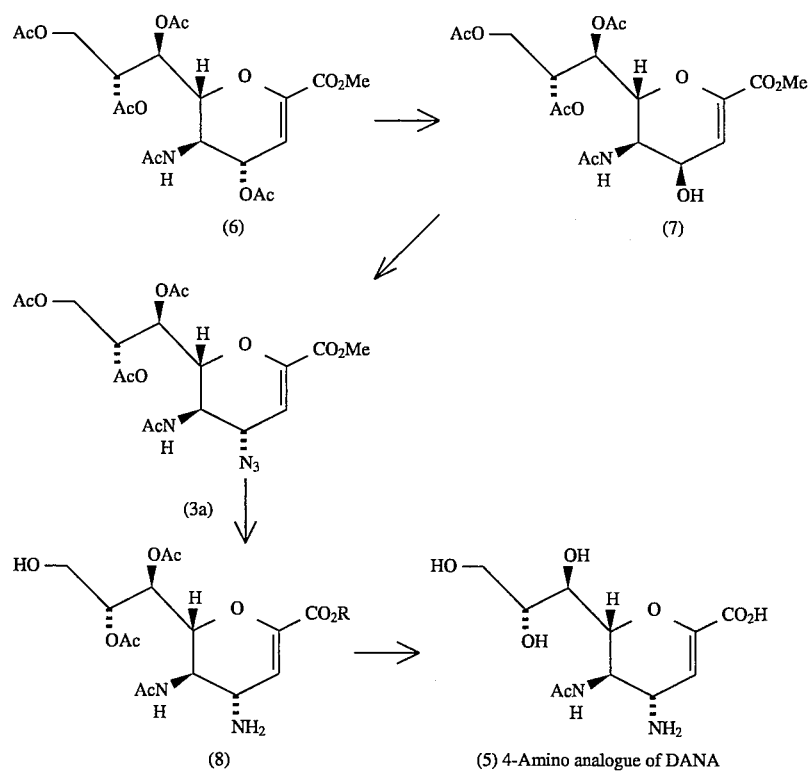
We claim:
1. A process for the preparation of a compound of formula
(III)

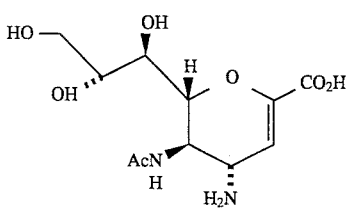

wherein Ac is acetyl
which comprises the steps of
(a) reacting a compound of formula (II)

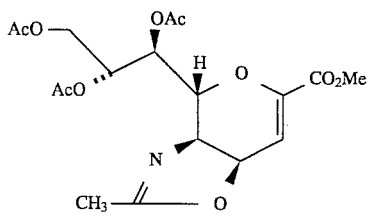

wherein Ac is acetyl
with trimethylsilylazide in a protic solvent to give a compound of formula (I);

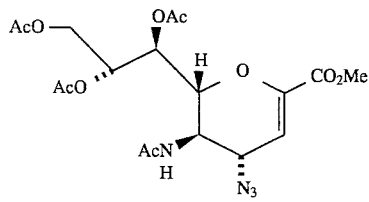

(b) hydrolyzing the compound of formula (I) to give a compound of formula (4a)

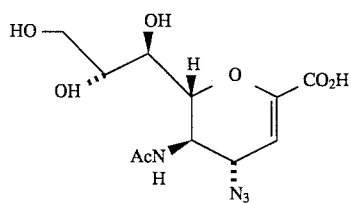

(c) hydrogenating the compound of formula (4a) or a protected derivative thereof in the presence of a poisoned catalyst followed by hydrolysis.

2. A process for the preparation of a compound of formula (I)

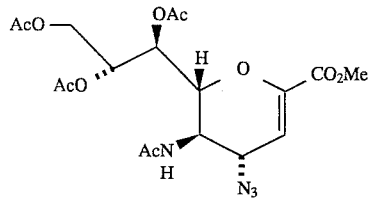

wherein Ac is acetyl,
which comprises reacting a compound of formula (II)

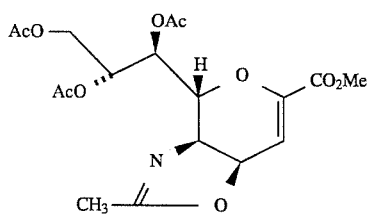

wherein Ac is acetyl with trimethylsilylazide in a protic solvent.

3. A process as claimed in claim 2 wherein the protic solvent is a $C_{1-8}$ alcohol.

4. A process as claimed in claim 2 wherein the reaction is carried out in tert-butyl alcohol.

5. A process as claimed in claim 2 wherein the trimethylsilylazide is present in an amount of 1 to 6 molar equivalents of the compound of formula (II).

6. A process as claimed in claim 2 wherein the molar ratio of trimethylsilylazide to the compound of formula (II) is from 1:1 to 2:1.

7. A process as claimed in claim 2 wherein the reaction is carried out at a temperature of from 0° to 150° C.

8. A process for the preparation of a compound of formula (III)

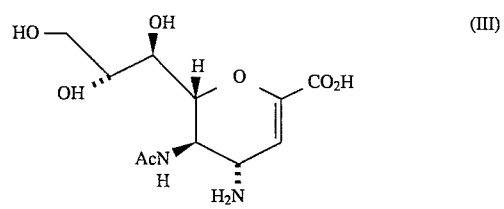

wherein Ac is acetyl,
which comprises catalytic hydrogenation of a compound of formula (IV)

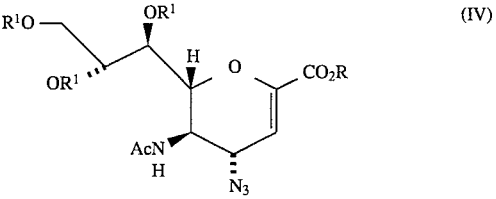

wherein Ac is acetyl, R is H or $C_{1-4}$ alkyl and $R^1$ is H or a hydroxyl protecting group, followed where required by hydrolysis.

9. A process as claimed in claim 8 wherein the compound of formula (IV)

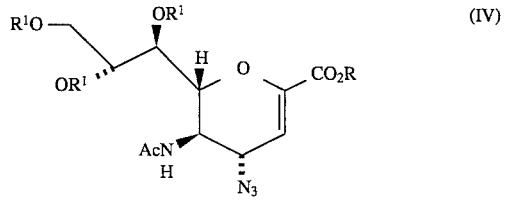

is obtained by reacting a compound of formula (IIa)

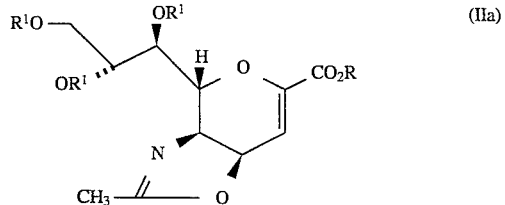

with trimethylsilylazide in a protic solvent.

10. A process as claimed in claim 8 wherein the catalyst is a poisoned catalyst.

11. A process as claimed in claim 8 wherein the catalyst is a poisoned palladium catalyst.

12. A process as claimed in claim 11 wherein the catalyst is a palladium catalyst poisoned with lead.

13. A process as claimed in claim 12 wherein the catalyst is a Lindlar catalyst.

14. A process as claimed in claim 8 which is carried out at a temperature of 0° to 50° C.

15. A process as claimed in claim 8 wherein in the compound of formula (IV) at least one of R and R' is not hydrogen and wherein the product of reduction is subsequently hydrolysed.

16. A process as claimed in claim 15 wherein the hydrolysis is effected in aqueous medium.

17. A process as claimed in claim 15 wherein the hydrolysis is effected with a base selected from triethylamine, an alkali metal hydroxide or an alkali metal carbonate.

* * * * *